United States Patent [19]

Wright et al.

[11] Patent Number: 4,929,780
[45] Date of Patent: May 29, 1990

[54] MULTISTAGE PROCESS FOR CONVERTING OXYGENATES TO LIQUID HYDROCARBONS AND ETHENE

[75] Inventors: Bernard S. Wright, East Windsor; Ronald M. Gould, Sewell; Hartley Owen, Belle Mead, all of N.J.

[73] Assignee: Mobil Oil Corporation, New York, N.Y.

[21] Appl. No.: 861,820

[22] Filed: May 12, 1988

[51] Int. Cl.⁵ .............................................. C07C 1/20
[52] U.S. Cl. .................................... 585/303; 585/324; 585/302; 585/327; 585/469; 585/301
[58] Field of Search ............... 585/312, 314, 315, 316, 585/324, 327, 469, 640, 733, 330, 301, 302, 303

[56] References Cited

U.S. PATENT DOCUMENTS

| | | | |
|---|---|---|---|
| 4,387,263 | 6/1983 | Vogt et al. | 585/640 |
| 4,450,311 | 5/1984 | Wright et al. | 585/413 |
| 4,482,772 | 11/1984 | Tabak | 585/330 |
| 4,497,968 | 2/1985 | Wright et al. | 585/304 |
| 4,504,691 | 3/1985 | Hsia et al. | 585/519 |
| 4,506,106 | 3/1985 | Hsia et al. | 585/312 |
| 4,511,747 | 4/1985 | Wright et al. | 585/415 |
| 4,543,435 | 9/1985 | Gould et al. | 585/330 |
| 4,547,602 | 10/1985 | Tabak | 585/314 |
| 4,579,999 | 4/1986 | Gould et al. | 585/312 |

FOREIGN PATENT DOCUMENTS 65112  5/1981  European Pat. Off. ............ 585/640

*Primary Examiner*—Asok Pal
*Attorney, Agent, or Firm*—Alexander J. McKillop; Charles J. Speciale; L. G. Wise

[57] ABSTRACT

An integrated process for converting methanol and other lower molecular weight oxygenates to gasoline and distillate range liquid hydrocarbons and ethene is disclosed. When it is desirable to increase ethene yield, an auxiliary methanol-to-olefins (MTO) fixed bed reactor unit is activated in conjunction with a continuously operated primary MTO fluidized bed reactor.

11 Claims, 2 Drawing Sheets

MULTISTAGE PROCESS FOR CONVERTING OXYGENATES TO LIQUID HYDROCARBONS AND ETHENE

BACKGROUND OF THE INVENTION

This invention relates to an integrated system for converting oxygenates, such as methanol or dimethyl ether (DME), to liquid hydrocarbons and ethene. In particular it provides a continuous process for producing hydrocarbon products by converting the oxygenate feedstock catalytically to an intermediate lower olefinic stream, separating the ethene and oligomerizing the remaining olefins to produce distillate and gasoline.

In order to provide an adequate supply of liquid hydrocarbons for use as synfuels or chemical feedstocks, various processes have been developed for converting coal and natural gas to gasoline, distillate and lubricants. A substantial body of technology has grown to provide oxygenated intermediates, especially methanol. Large scale plants can convert methanol or similar aliphatic oxygenates to liquid fuels, especially gasoline. However, the demand for heavier hydrocarbons has led to the development of processes for increasing yield of diesel fuel by a multi-stage technique.

Recent developments in zeolite catalysts and hydrocarbon conversion processes have created interest in utilizing olefinic feedstocks for producing $C_5^+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2-C_5$ alkenes. This process may supplant conventional alkylation units. In U.S. Pat. Nos. 3,960,978 and 4,021,502, Plank, Rosinski and Givens disclose conversion of $C_2-C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5^+$ aliphatic and aromatic hydrocarbons. Olefinic gasoline is produced in good yield by the MOGD process and may be recovered as a product or recycled to the oligomerization reactor system for further conversion to distillate-range products. Operating details for typical MOGD units are disclosed in U.S. Pat. Nos. 4,445,031, 4,456,779 (Owen et al) and 4,433,185 (Tabak), incorporated herein by reference.

In addition to their use as shape selective oligomerization catalysts, the medium pore ZSM-5 type catalysts are useful for converting methanol and other lower aliphatic alcohols or corresponding ethers to olefins. Particular interest has been directed to a catalytic process ("MTO") for converting low cost methanol to valuable hydrocarbons rich in ethene and $C_3^+$ alkenes. Various processes are described in U.S. Pat. Nos. 3,894,107 (Butter et al), 3,928,483 (Chang et al), 4,025,571 (Lago), 4,423,274 (Daviduk et al) and 4,547,616 (Avidan et al), incorporated herein by reference. It is known that the MTO process can be optimized by fluidized bed catalysis to produce a major fraction of $C_2-C_4$ olefins economically.

It has been found that ethene production can be increased by supplementing a continuous fluidized bed unit with a smaller capacity fixed bed unit. In U.S. Pat. No. 4,506,106 (Hsia et al), incorporated herein by reference, there is disclosed a method for increasing the ethene production by employing a fixed bed reactor operated within a specified range of conditions. The ethene may be recovered in an interstage sorption unit as a valuable chemical feedstock, while the remaining olefins are oligomerized to predominantly $C_{10}-C_{20}$ liquid hydrocarbons. Oligomerization process conditions tend to convert only a small portion of ethene as compared to $C_3^+$ olefins.

SUMMARY OF THE INVENTION

It has been discovered that methanol, DME or the like may be converted to liquid fuels, particularly distillate, in a multi-stage continuous process, with integration between the major process units to provide an increase in ethene production on demand. The additional ethene is obtained from an intermittently-operated auxiliary MTO conversion unit. The major MTO conversion unit is operated in substantially continuous use under steady state conditions. Process conditions in the auxiliary unit allow for a significantly higher percentage of ethene in the $C_2-C_4$ olefin fraction from the oxygenate conversion reaction. When both units are on stream, the ethene production is maximized. However, a fixed bed oxygenate conversion unit requires maintenance shutdown for in situ catalyst regeneration offstream. This is usually a planned periodic interruption. The primary MTO process hydrocarbon effluent stream, after water and an ethene rich stream and $C_5^+$ liquid hydrocarbons are recovered, can be fed to the MOGD stage for conversion to heavier hydrocarbons. Part of the oligomerization stage gasoline rich product may be recycled to the sorption fractionation unit.

In a preferred embodiment, the invention provides methods for an integrated continuous technique for converting oxygenated organic feedstock to liquid hydrocarbons and ethene comprising means for reacting a major portion of feedstock comprising one or more lower aliphatic organic compounds in a primary conversion unit comprising a low pressure fluidized bed reactor containing zeolite oxygenate conversion catalyst to dehydrate and convert at least a portion of the feedstock to hydrocarbons containing a major fraction of $C_2-C_4$ olefins having less than 10% by weight ethene and a minor fraction of $C_5^+$ heavy hydrocarbons; intermittently reacting a minor portion of the lower aliphatic oxygenate feedstock in an auxiliary conversion unit comprising a lower pressure fixed bed reactor containing an acidic zeolite catalyst to dehydrate and convert at least a portion of the feedstock to hydrocarbons containing a major fraction of $C_2-C_4$ olefins having at least 15% by weight ethene and a minor fraction of $C_5^+$ heavy hydrocarbons, thereby increasing ethene production; cooling and separating the effluent from the primary conversion unit to provide an aqueous liquid stream, a heavy hydrocarbon liquid stream, and recovering a primary light hydrocarbon vapor stream rich in $C_2-C_4$ olefins; cooling and separating the effluent from the auxiliary conversion unit to provide an aqueous liquid stream, a heavy hydrocarbon liquid stream, and recovering an auxiliary light hydrocarbon vapor stream rich in ethene; combining and fractionating the primary and auxiliary light hydrocarbon vapor streams by compressing and selectively sorbing $C_3+$ hydrocarbons in a gasoline sorbent stream to recover an ethene-rich vapor stream and a liquid stream rich in $C_3+$ sorbate; and contacting the sorbate-rich stream in a reaction zone with a shape selective medium pore zeolite oligomerization catalyst at elevated temperature and pressure to convert olefins to an oligomerization effluent stream comprising olefinic gasoline and distillate range liquids. The oligomerization effluent stream is separated to obtain a distillate fraction, a gasoline fraction, and a lighter hydrocarbon fraction.

Advantageously, the oxygenate conversion and the oligomerization catalysts comprise acidic ZSM-5 type zeolites and at least a portion of the gasoline fraction is employed as the sorbent stream.

Other objects and features of the invention will be seen in the following description and drawings.

THE DRAWINGS

DESCRIPTION OF PREFERRED EMBODIMENTS

Numerous oxygenated organic compounds may be contained in the feedstock material to be converted in the major and auxiliary MTO units. Since methanol or its ether derivative (DME) are industrial commodities available from synthesis gas or the like, these materials are utilized in the description herein as preferred starting materials. It is understood by those skilled in the art that MTO-type processes can employ methanol, dimethyl ether and mixtures thereof, as well as other aliphatic alcohols, ethers, ketones and/or aldehydes. It is known in the art to partially convert oxygenates by dehydration, as in the catalytic reaction of methanol over gamma-alumina to produce DME intermediate. Typically, an equilibrium mixture ($2CH_3OH \rightleftharpoons CH_3OCH_3 + H_2O$) is produced by partial dehydration. This reaction takes place in either conversion of methanol to lower olefins (MTO) or methanol to gasoline (MTG).

Catalyst versatility permits the same zeolite to be used in both the primary conversion stage (MTO) and secondary oligomerization stage (MOGD). While it is within the inventive concept to employ substantially different catalysts in these stages, it is advantageous to employ a standard ZSM-5 having a silica alumina molar ratio of 70:1.

The oligomerization catalysts preferred for use herein include the crystalline aluminosilicate zeolites having a silica to alumina ratio of at least 12, a constraint index of about 1 to 12 and acid cracking activity of about 160–200. Representative of the ZSM-5 type zeolites are ZSM-5, ZSM-11, ZSM-12, ZSM-22, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable catalyst for fixed bed operation is HZSM-5 zeolite with 35 wt. % alumina binder in the form of cyclindrical extrudates of about 1–5 mm. These medium pore shape selective catalysts are sometimes known as porotectosilicates or "pentasil" catalysts.

Other catalysts and processes suitable for converting methanol/DME to lower olefins are disclosed in U.S. Pat. No. 4,393,265 (Bonifaz), U.S. Pat. No. 4,387,263 (Vogt et al.) and European Patent Application No. 0081683 (Marosi et al.), and ZSM-45. In addition to the preferred aluminosilicates, the borosilicate, ferrosilicate and "silicalite" materials may be employed. ZSM-5 type catalysts are particularly advantageous because the same material may be employed for dehydration of methanol to DME, conversion to lower olefins and oligomerization.

In this description, metric units and parts by weight are employed unless otherwise stated.

Figure 1:
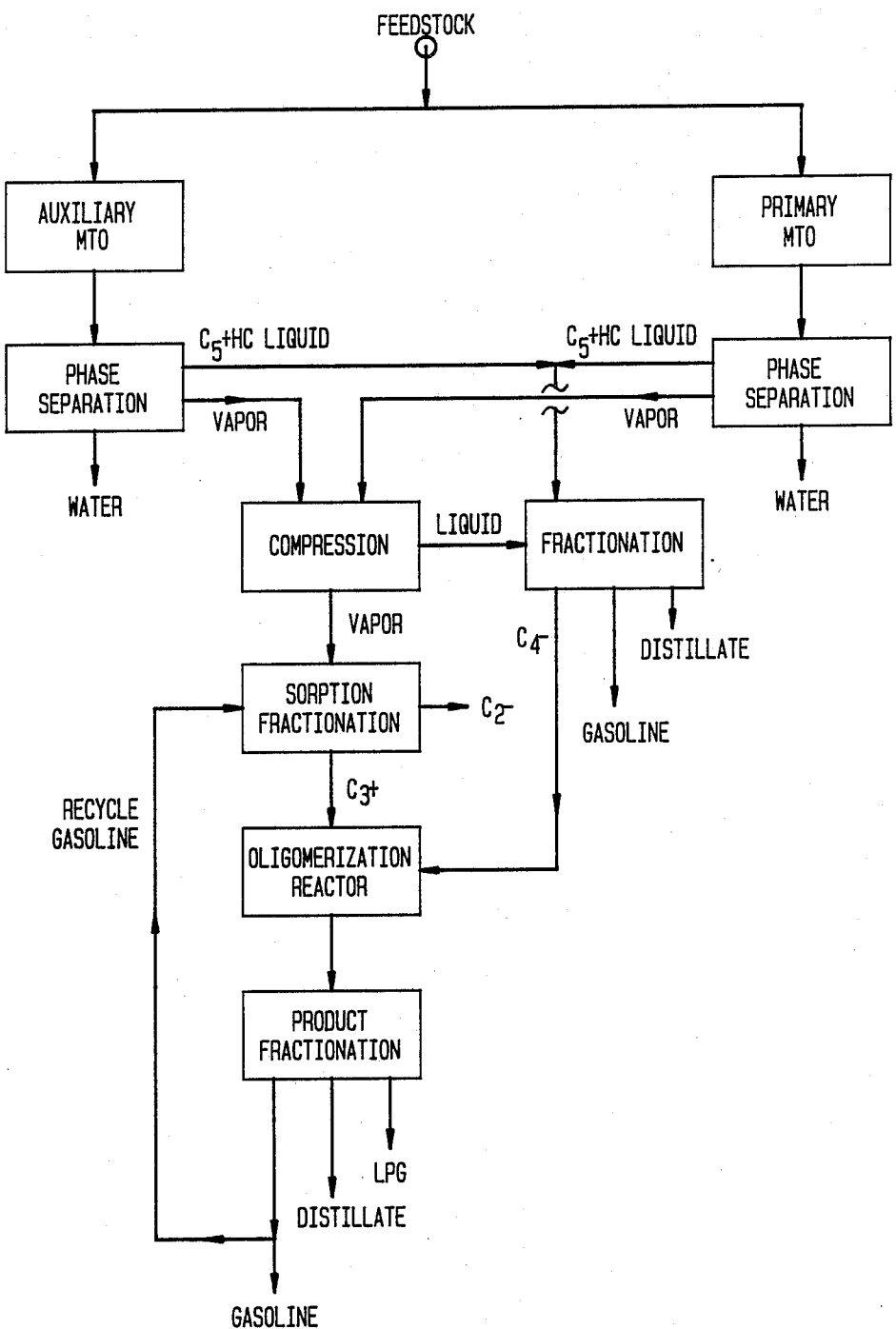
FIG. 1 is a process flow sheet showing the major unit operations and process streams.

Referring to FIG. 1, a major portion of feedstock (methanol or DME, for instance) is fed to the primary conversion unit where it is converted to lower olefins and gasoline hydrocarbon plus water by dehydration of the oxygenated feedstock. Byproduct water is recovered by simple phase separation from the cooled effluent. Liquid hydrocarbons consisting essentially of $C_5+$ gasoline range materials is recovered by fractionation. At least a portion of the vapor phase effluent from the primary conversion unit is compressed and heated along with oligomerization stage recycle gasoline sorbent and throughput liquids to oligomerization reaction temperature, and the combined olefinic stream is reacted at high pressure and elevated temperature over the shape selective medium pore zeolite catalyst. Effluent is then separated into light gases, $C_5+$ gasoline, at least a portion of which can be recycled to the absorption zone, and distillate range products. The distillate stream comprises a major fraction of $C_{10}$–$C_{20}$ high boiling aliphatics and may contain a minor amount of aromatics.

A minor portion of the oxygenate feedstock is converted to a predominantly ethene-rich lower olefins product in a low pressure fixed bed auxiliary reaction zone to increase ethene production on demand. About 25 to 90% of the methanol feedstock is converted in the auxiliary unit per reactor pass. Diluent water may be cofed with methanol and/or dimethyl ether in a molar ratio of about 0.1:1 to 5:1, based on methanol equivalents.

The ethene-rich lower olefins from the auxiliary reactor zone are recovered as a low pressure gas and combined with the primary MTO unit olefinic gas stream for recovery of increased ethene and upgrading $C_3+$ olefins by oligomerization. The $C_5+$ hydrocarbons from the auxiliary MTO unit is combined with the $C_5+$ hydrocarbons from the primary unit and compression liquid from both units. The combined streams are fractionated to separate a $C_5+$ product gasoline, $C_9+$ product distillate and a $C_4-$ stream for oligomerization.

In the process for catalytic conversion of olefins to heavier hydrocarbons by catalytic oligomerization using an acid crystalline zeolite, such as ZSM-5 type catalyst, process conditions can be varied to favor the formation of either gasoline or distillate range products. At moderate temperature and relatively high pressure, the conversion conditions favor distillate range product having a normal boiling point of at least 154° C. (310°

F.). Lower olefinic feedstocks containing $C_2$-$C_6$ alkenes may be converted selectively; however, the distillate mode conditions do not convert a major fraction of ethylene. While propene, butene-1 and others may be converted to the extent of 50 to 99% in the distillate mode, only about 10 to 50% of the ethene component will be converted.

When the catalytic oligomerization of lower olefins is conducted at moderate temperature and relatively high pressure, i.e., conditions which favor distillate range products, the ethene is preferably recovered prior to the oligomerization reactor since it is unreactive as compared to the propenes and other lower olefins.

Figure 2:
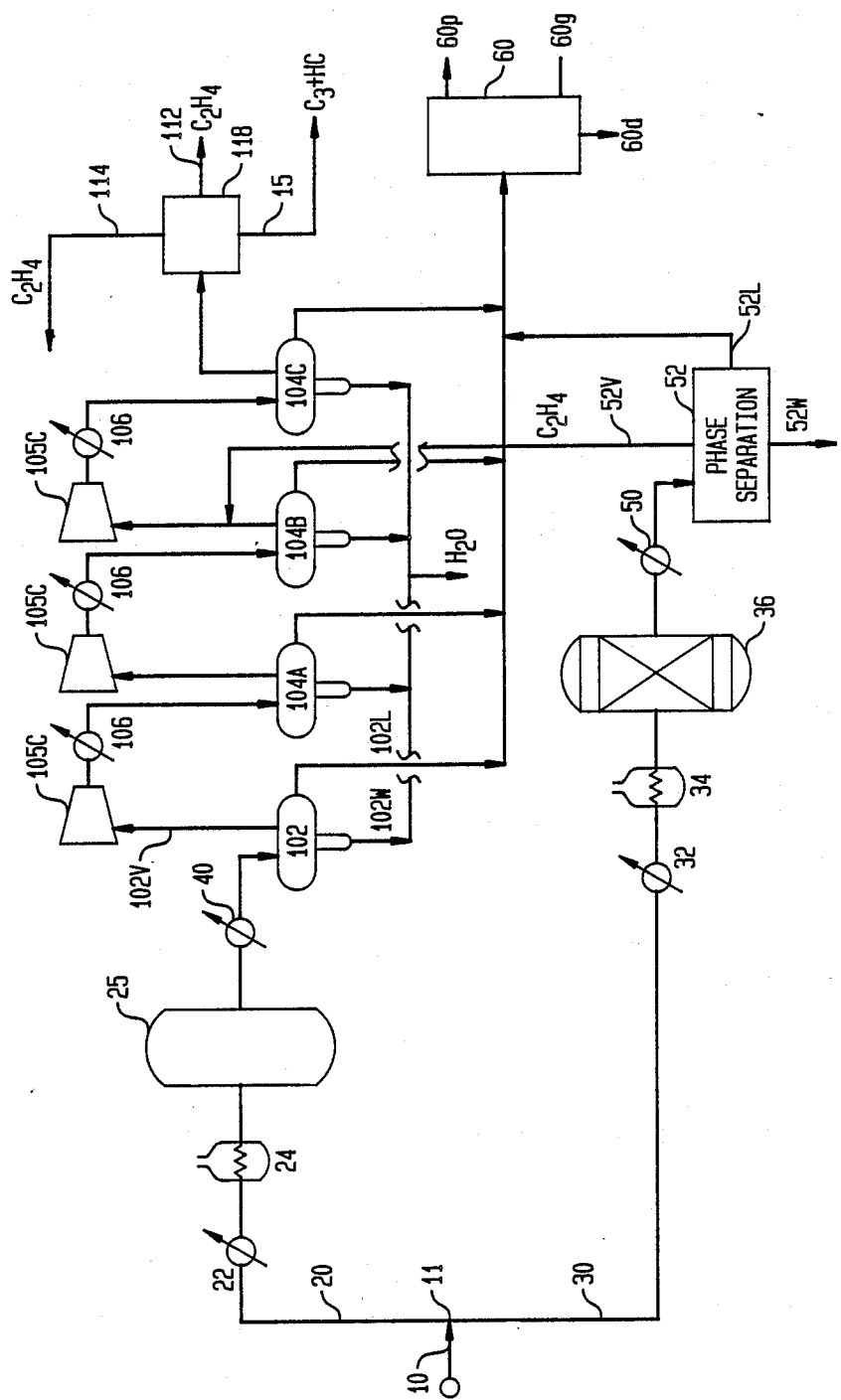
FIG. 2 is a preferred embodiment of an integrated olefins upgrading process.

The integrated system of a primary fluidized bed MTO conversion unit and an auxiliary fixed bed MTO conversion unit is depicted in FIG. 2. The oxygenate feedstock, which is preferably a mixture of methanol and dimethylether from an acid catalyzed dehydration reaction, is passed via conduit 10 to a valve 11, where a major portion of the feedstock is conducted through line 20 and is passed through process heat exchange unit 22 and then furnace 24 to achieve the temperature for catalytic conversion in fluidized bed reactor 25.

The reactor effluent is sequentially compressed and cooled by passing through heat exchange unit 40. Cooled effluent enters phase separator 102 to provide a vapor stream 102V, rich in $C_2$-$C_4$ olefins, a liquid hydrocarbons stream 102L, and by-product water stream 102W. The liquid (eg-$C_5^+$) stream 102L is combined with a corresponding liquid HC from succeeding separators and sent to fractionation unit 60. The vapor stream 102V is polytropically compressed by multistage compressor set 105C, cooled via exchanger 106 and passed to a succeeding separator 104A, at which point the preceeding phase separation technique is repeated. Likewise other separators 104B and 104C operate to provide an ethene-rich stream 104V, which is passed to ethylene recovery unit 118. As is understood by one skilled in the art, ethene can be treated in a cryogenic plant cold box, de-ethanizer tower, absorption unit or the like to remove undesirable components prior to recycle 114 and/or recovery 112. A suitable selective sorption unit is disclosed in U.S. Pat. No. 4,471,147 (Hsia et al), incorporated herein by reference. Preferably, compressed light hydrocarbons are fractionated to recover a recycle stream containing at least 90 mole percent ethene. This can be achieved by selectively absorbing $C_3^+$ components in a $C_5^+$ liquid hydrocarbon sorbent stream and then recovering the ethylene in a cryogenic unit. Advantageously, the MTO effluent is received at about atmospheric pressure (e.g., 100-150 kPa) and compressed in plural stages to an intermediate pressure of about 1100-3500 kPa (150-400 psig) and separated in the final vessel 104C at about ambient temperature (20°-60° C.).

On demand, a minor portion of the lower oxygenate feedstock is fed through line 30 and is passed through process heat exchange unit 32 and furnace 34 to achieve the temperature for catalytic conversion in fixed bed reactor 36. The auxiliary conversion unit is operated in the temperature range of about 260° C. to 425° C., in the pressure range of about 170 to 800 kPa, and in the weight hourly space velocity range of about 0.5 to 1.0 based on zeolite equivalent catalyst and methanol equivalent in the feedstock.

The reactor effluent is cooled by passing through heat exchange unit 50. Effluent then undergoes phase separation in separator unit 52 to provide a vapor stream 52V, rich in $C_2$-$C_4$ olefins and containing at least 15% by weight ethene, a liquid hydrocarbon stream 52L, and by-product water stream 52W. The vapor stream 52V is passed to the third stage of the primary MTO unit compressor 106, and then to phase separator 104C where the amount of ethene which passes through line 104V and to ethylene unit 118 is substantially increased. Hydrocarbon stream 52L is combined with stream 102L and fractionated in unit 60 to provide $C_5^+$ gasoline 60g, $C_9^+$ distillate 60d, and $C_4^-$ olefins 60p.

The combined processes are an effective means for converting oxygenated organic compounds, such as methanol, DME, lower aliphatic ketones, aldehydes, esters, etc., to valuable hydrocarbon products and ethene. Thermal integration is achieved by employing heat exchangers between various process streams, towers, absorbers, etc.

In a preferred embodiment, a crude methanol feed is processed in an integrated MTO-MOGD system with continuous primary fluidized bed and auxiliary fixed bed MTO reactors. The auxiliary fixed bed reactor processes about 25-30% of the methanolic feed on demand. Operation of this system results in a doubling of the net ethylene recovery, as compared to an integrated MTO-MOGD system with a single fluidized bed MTO unit. The yields of pressurized gasoline and blended distillate are similar for both systems. The following table compares the net product yield for these integrated plants.

Table I gives a comparison of the standard and the improved MTO-MOGD integrated systems.

TABLE I

| | MTO-MOGD-ALKYLATION UNIT INTEGRATION | MTO-MOGD-ALKYLATION UNIT INTEGRATION WITH "AUXILIARY" MTO REACTOR |
|---|---|---|
| Unpressurized Gasoline (B/SD), barrels per day | 8595 | 7857 |
| Butanes for Pressurizing (B/SD) | 348 | 585 |
| Blended Distillate (B/SD) | 8939 | 8449 |
| Ethylene (thousand metric tonnes/yr.) (delivered after purification in cryogenic unit with 98% recovery) | 43.9 | 85.9 |

A further advantage may be achieved in the manufacture of valuable byproducts, particularly durene. The auxiliary MTO unit 36 produces alkyl aromatics, which may be recovered by fractionating liquid stream 52L, which may contain more than 25 wt % durene, recoverable from other $C_8$-$C_{10}$ aromatics by crystallization.

Various modifications can be made to the system, especially in the choice of equipment and non-critical processing steps. While the invention has been described by specific examples, there is no intent to limit the inventive concept as set forth in the following claims.

We claim:

1. An integrated continuous process for converting oxygenated organic feedstock to liquid hydrocarbons and ethene, comprising the steps of:

reacting a major portion of feedstock comprising lower aliphatic oxygenate in a continuous primary conversion unit comprising a low pressure fluidized bed reactor containing zeolite oxygenate conversion catalyst to dehydrate and convert at least a portion of the feedstock to hydrocarbons containing a major fraction of $C_2$–$C_4$ olefins having less than 10% by weight ethene and a minor fraction of $C_5+$ heavy hydrocarbons;

intermittently reacting a minor portion of the lower aliphatic oxygenate feedstock in the presence of a diluent under partial conversion conditions to convert about 25 to 90% of feedstock per pass in an auxiliary conversion unit comprising a low pressure fixed bed reactor containing an acidic zeolite catalyst to dehydrate and convert at least a portion of the feedstock to hydrocarbons containing a major fraction of $C_2$–$C_4$ olefins having at least 15% by weight ethene and a minor fraction of $C_5+$ heavy hydrocarbons, thereby increasing ethene production;

cooling and separating reactor effluent from the primary conversion unit to provide an aqueous liquid stream, a heavy hydrocarbon liquid stream, and recovering a primary light hydrocarbon vapor stream rich in $C_2$–$C_4$ olefins;

cooling and separating reactor effluent from the auxiliary conversion unit to provide an aqueous liquid stream, a heavy hydrocarbon liquid stream, and recovering an auxiliary light hydrocarbon vapor stream rich in ethene;

combining the primary and auxiliary light hydrocarbon vapor streams, compressing and selectively sorbing $C_3+$ vapor hydrocarbons in a gasoline sorbent stream to recover an ethene-rich vapor stream and a liquid stream rich in $C_3+$ sorbate; and contacting the sorbate-rich streams in a reaction zone with a shape selective medium pore zeolite oligomerization catalyst at elevated temperature and pressure to convert olefins to an oligomerization effluent stream comprising olefinic gasoline and distilled range liquids.

2. The process of claim 1 wherein the oligomerization effluent stream is separated to obtain a distillate fraction, a gasoline fraction, and a lighter hydrocarbon fraction.

3. The process of claim 2 wherein at least a portion of the gasoline fraction is employed as the sorbent stream, and wherein compressed liquid recovered from the primary and auxiliary reactor effluent vapor streams are combined for coprocessing prior to fractionation.

4. The process of claim 1 wherein the zeolite oxygenate conversion catalyst comprises ZSM-5 type zeolite.

5. The process of claim 1 wherein the shape selective medium pore zeolite oligomerization catalyst comprises HZSM-5 type zeolite.

6. The process of claim 1 wherein the auxiliary conversion unit is operated in the temperature range of about 260° C. to 425° C., in the pressure range of about 170 to 800 kPa, and in the weight hourly space velocity range of about 0.5 to 1.0 based on zeolite equivalent catalyst and methanol equivalent in the feedstock.

7. The process of claim 6 wherein about 25 to 90% of methanol feedstock is converted in the auxiliary unit per reactor pass and wherein water diluent is cofed with methanol and/or dimethyl ether in a molar ratio of about 0.1:1 to 5:1, based on methanol equivalents.

8. The process of claim 1 wherein the lower aliphatic oxygenate feedstock comprises methanol, dimethyl ether, or mixtures thereof.

9. In the process of producing liquid hydrocarbons from oxygenate feedstock containing methanol and/or dimethyl ether by converting the oxygenate feedstock in a fluidized bed primary reaction zone in contact with zeolite oxygenate conversion catalyst to provide a first olefinic gas stream rich in $C_2$–$C_4$ olefins and containing less than 10 wt. % ethene, wherein the ethene is recovered from the gas stream by compressing the gas stream and selectively absorbing the $C_3+$ olefins from the compressed gas stream to provide a liquid $C_3+$ stream rich in lower olefins, and wherein the liquid $C_3+$ olefinic stream is pressurized and contacted with acidic shape selective medium pore zeolite oligomerization catalyst to upgrade lower olefins to liquid hydrocarbons comprising distillate and gasoline products; the improvement which comprises:

partially converting a minor portion of the oxygenate feedstock predominantly to ethene-rich lower olefins in the presence of a diluent in a low pressure fixed bed auxiliary reactor zone containing acidic zeolite catalyst and operated to increase ethene production on demand;

recovering the ethene-rich lower olefins from the auxiliary reactor zone as a low pressure gas and combining the ethene-rich lower olefins with the first olefinic gas stream for combined recovery of increased ethene production and upgrading $C_3+$ olefins by oligomerization; and periodically interrupting feed to the auxiliary reactor zone and regenerating the fixed bed catalyst in situ and off stream from oxygenate conversion.

10. The process of claim 9 wherein the auxiliary reactor zone contains HZSM-5 type zeolite catalyst.

11. The process of claim 9 wherein the auxiliary reactor zone is operated in the temperature range of about 260° C. to 425° C. in the pressure range of about 170 to 800 kPa, and in the weight hourly space velocity range of about 0.5 to 1.0 based on zeolite equivalent catalyst and methanol equivalent in the feedstock.

* * * * *